(12) United States Patent
Hubbell et al.

(10) Patent No.: US 7,427,410 B2
(45) Date of Patent: Sep. 23, 2008

(54) COATING HYDROPHOBIC SURFACES WITH AMPHIPHILIC THIOETHERS TO REDUCE PROTEIN ADSORPTION AND CELL ADHESION

(75) Inventors: Jeffrey A. Hubbell, Zurich (CH); Jane P. Bearinger, Livermore, CA (US); Alessandro Napoli, Zurich (CH); Marcus Textor, Schaffhausen (CH); Nicola Tirelli, Uster (CH)

(73) Assignee: Ecole Polytechnique Federale de Lausanne (EPFL), Lausanne (CH)

( * ) Notice: Subject to any disclaimer, the term of this patent is extended or adjusted under 35 U.S.C. 154(b) by 336 days.

(21) Appl. No.: 10/246,362

(22) Filed: Sep. 18, 2002

(65) Prior Publication Data

US 2003/0133963 A1 Jul. 17, 2003

Related U.S. Application Data

(60) Provisional application No. 60/323,353, filed on Sep. 18, 2001.

(51) Int. Cl.
*A61F 2/00* (2006.01)
*A61K 38/43* (2006.01)
*C12N 11/08* (2006.01)

(52) U.S. Cl. ............... 424/423; 424/94.1; 435/180
(58) Field of Classification Search ............... None
See application file for complete search history.

(56) References Cited

U.S. PATENT DOCUMENTS

| | | | |
|---|---|---|---|
| 4,795,660 A | 1/1989 | Cooray et al. | |
| 5,030,352 A | 7/1991 | Varady et al. | |
| 5,688,855 A | 11/1997 | Stoy et al. | |
| 5,821,343 A | 10/1998 | Keogh | |
| 5,863,650 A * | 1/1999 | Healy et al. | 428/336 |
| 6,306,165 B1 | 10/2001 | Patnaik et al. | |
| 6,358,557 B1 | 3/2002 | Wang et al. | |
| 6,562,398 B1 | 5/2003 | Braach-Maksvytis et al. | |
| 6,958,212 B1 * | 10/2005 | Hubbell et al. | 435/6 |
| 7,091,127 B2 * | 8/2006 | Hubbell et al. | 438/704 |
| 7,132,475 B2 * | 11/2006 | Hubbell et al. | 525/93 |

FOREIGN PATENT DOCUMENTS

WO  WO 03/024186  3/2003

OTHER PUBLICATIONS

Stouffer et al., Macromolecules, 1988, 21, 1204-1208.*
Bearinger, et al. PPS-PEG Block Copolymers Render Hydrophobic Surfaces Protein and Cell Resistant, European Cells and Materials vol. 2, Suppl. 1, 2001 (p. 45).
Libioulle, et al. Contact-Inking Stamps for Microcontact Printing of Alkanethiols on Gold, Langmuir, 1999, 15:300-304.
Nuzzo, et al. Fundamental Studies of the Chemisorption of Organosulfur Compounds on Au(111). Implications for Molecular Self-Assembly on Gold Surfaces, Journal of the American Chemical Society. 1987. 109:733-740.
Nuzzo, et al. Adsorption of Bifunctional Organic Disulfides on Gold Surfaces. Journal of the American Chemical Society, 1983, 105:4481-4483.
Tam-Chang, et al. Self-Assembled Monolayers on Gold Generated from Alkanethiols with the Structure $RNHCOCH_2SH$, Langmuir, 1995, 11:4371-4382.

* cited by examiner

*Primary Examiner*—David M Naff
(74) *Attorney, Agent, or Firm*—Kristina Bieker-Brady; Clark & Elbing LLP

(57) ABSTRACT

The present invention provides methods and apparatus for coating surfaces with specially designed thioethers and amphiphilic thioethers that reduce protein adsorption and/or cell adhesion. This reduction may be achieved, for example, by controlling the spacing or length of pendant chains or hydrophilic blocks in an amphiphilic thioether. Techniques for determining spacing include adsorbing the thioether from a solution or a colloidal suspension, or controlling the degree of polymerization of the thioether. Techniques for controlling the length of the pendant chains include controlling the degree of polymerization of the pendant chains. Multiblock copolymers of poly(propylene sulfide) and poly(ethylene glycol) ("PPS-PEG") represent an exemplary family of amphiphilic thioethers. Methods for coating surfaces with amphiphilic thioethers are also provided.

22 Claims, 8 Drawing Sheets

FIGS. 10 A-J
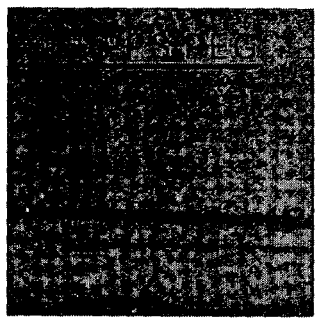 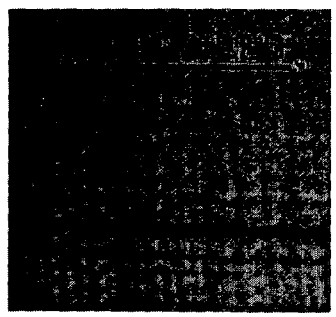 
hydrophobic substrates
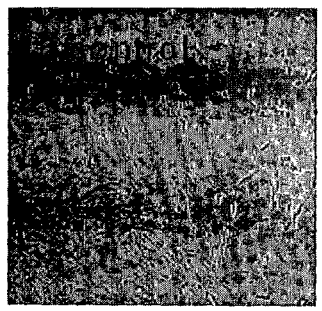 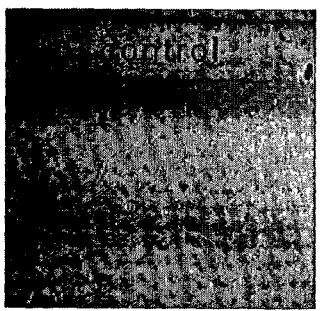 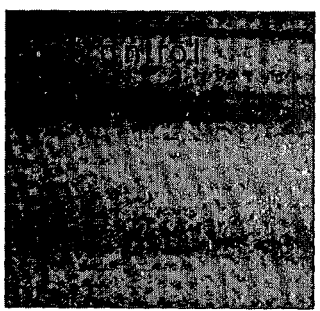
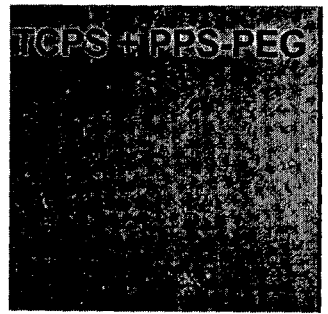 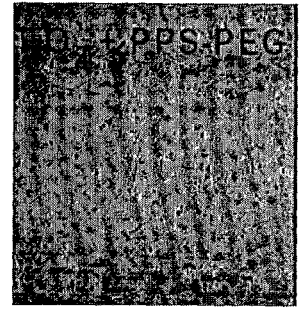
hydrophilic substrates
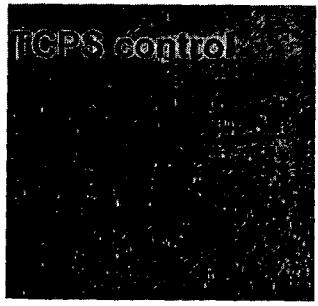 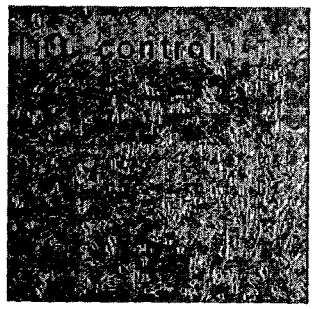

COATING HYDROPHOBIC SURFACES WITH AMPHIPHILIC THIOETHERS TO REDUCE PROTEIN ADSORPTION AND CELL ADHESION

CROSS-REFERENCE TO RELATED APPLICATIONS

This application claims benefit of priority to U.S. Provisional Application No. 60/323,353, filed Sep. 18, 2001, hereby incorporated by reference.

BACKGROUND OF THE INVENTION

The present invention relates to the field of surface coatings that are useful for reduction of protein adsorption and/or cell adhesion and for presentation of binding ligands.

Numerous methods can be used to coat surfaces. Hydrophobic interaction between block copolymers may be used to coat hydrophobic surfaces for subsequent use in aqueous environments. Examples of copolymers include block copolymers of polyethylene glycol blocks as a hydrophile and polypropylene glycol blocks as a hydrophobe. These materials adsorb upon the hydrophobic surface, with the strength of the interaction depending, for example, upon the hydrophobicity of the substrate, the hydrophobicity of the adsorbing block, the method of preparation of the interface, or the existence of any specific interactions between the adsorbing block and the hydrophobic substrate. The strength of the interaction is often not as strong as desired.

Chemisorption of thiols, disulfides, and derivatives thereof can be used to induce stable adsorption on metal surfaces, such as gold, silver, and copper. Thiols, alkane thiols, disulfides, and derivatives thereof, typically form a coating of close-packed independent chains when chemisorbed to a surface. Applications of thiol or disulfide surface coatings include, for example, corrosion prevention, adhesion promoters for organic coatings, lubrication, presentation of different chemical functional groups to an interface, surface patterning, and alteration of surface energetics. Common thiols, alkane thiols, and disulfides include octadecanethiol, hexadecanethiol, ω-oligo(ethyleneglycol) alkane thiols, and dimethyl disulfide. These materials are typically applied to surfaces, such as gold, silver, or copper from solution, e.g., ethanol or hexane.

When chemisorbed as a surface coating, the spacing of pendant chains, extending from the thiol or the disulfide sulfur atom(s), is typically dictated by the interaction of sulfur with the surface, e.g., gold, silver, or copper. This dictated spacing is a significant drawback in some applications, as the resistance afforded to protein adsorption may not be sufficient. The surface coverage of pendant chains also may be difficult to control. Additionally, alkane thiols are not very kinetically inert, i.e., replacement by other interactive molecules is likely to occur at defects of the coating upon long-term exposure to such molecules.

In view of the foregoing, there is a need for new types of coatings that bind strongly to a surface, are kinetically inert, and provide flexibility in the density of pendant groups.

SUMMARY OF THE INVENTION

In one aspect, the present invention features a thioether surface coating on a hydrophobic substrate. In one embodiment, a surface coating including an amphiphilic poly or oligo (thioether) on a hydrophobic substrate covers the surface with a polymer layer displaying hydrophilic polymers or polymeric blocks at a water interface.

In a related aspect, the invention features a method of coating a surface that includes coating the surface with an amphiphilic thioether. The thioether includes at least one hydrophilic pendant group, and the identity, spacing, length, or density of the pendant group causes a reduction in protein adsorption or cell adhesion relative to an uncoated surface.

For the purposes of the present invention, the term "thioether" encompasses poly or oligo(thioethers). Multiblock copolymers of propylene sulfide ("PS") and ethylene glycol ("EG"), e.g., poly(propylene sulfide)-poly(ethylene glycol) ("PPS-PEG") copolymers, represent an exemplary family of amphiphilic poly(thioethers) and are disclosed, for example, in U.S. application Ser. No. 10/047,404, filed Oct. 19, 2001, now U.S. Pat. No. 7,132,475. The thioether block may serve several possible functions. In various embodiments, the blocks are designed to be very hydrophobic and thus lead to strong adsorption to hydrophobic surfaces with high stability in polar solvents (e.g., water and alcohols). When bound to surfaces such as gold, silver, or copper, thioethers exhibit binding strengths comparable to thiols and may be used to modify such surfaces.

Poly or oligo(thioether)s may include multiple sulfur atoms along their backbone chains, which are typically hydrophobic. This characteristic is in strong contrast to homologous poly(ethers). Pendant chains, which commonly may be attached at the ends of a poly(thioether) block, may be of any chemistry. In various embodiments, the hydrophobicity of the backbone and the affinity of sulfur for metals such as gold, silver, and copper enable stable deposition of thioethers on a variety of substrates, such as these metals, as well as hydrophobic substrates of a very wide range of compositions, e.g., tetrafluoroethylene polystyrene, hydrophobic silane-treated inorganic oxides, and essentially any other hydrophobic surface. If desired, these properties can be tailored by the use of different side chains in the thioether repeating unit. The thioethers may be adsorbed on a surface from a solution or colloidal suspension. The medium used in the adsorption determines, in part, the properties, e.g., surface density, of the thioether on the surface. In another embodiment, the thioether is disposed on the surface as disclosed in U.S. Provisional Application No. 60/323,355, filed Sep. 18, 2001 and U.S. application Ser. No. 10/246,500, filed Sep. 18, 2002, now U.S. Pat. No. 7,091,127 entitled "Methods and Apparatus for Patterning a Surface."

The coatings typically reduce protein adsorption or cell adhesion or both on a surface. This reduction may be controlled, for example, by the spacing and/or length of pendant chains. In particular, pendant chains are desirably anionic or nonionic water soluble polymers, e.g., poly(ethylene glycol) or poly(vinylpyrrolidone). The surface coating may reduce the amount of adsorbed protein or cells by at least 20, 30, 40, 50, 60, 70, 80, 90, or 95% relative to a control surface without the surface coating, as measured using standard methods (see, for example, Ausubel et al., *Current Protocols in Molecular Biology*, John Wiley & Sons, New York, 2000 and the surface plasmon resonance, x-ray photoelectron spectroscopy, and the OWLS methods described herein).

The surface coatings of the invention may also present a bioactive moiety. The moiety is, for example, covalently linked to a thioether. In one embodiment, the bioactive active moiety is released from the surface coating with a half-life of between 1 hour and 1 year, 1 day and 1 year, 1 month and 1 year, or 1 month and 6 months, at pH 7.4 and 37° C. The moiety may be linked to the thioether by an amide or ester bond. The moiety may also be linked by a non-hydrolysable bond, such as an ether linkage. Exemplary bioactive moieties include an organic compound, a nucleic acid, a protein, an enzyme substrate, an enzyme inhibitor, or an antibody.

In various embodiments of any of the above aspects, the surface coating is adsorbed onto the surface of a medical device such as a catheter or an artificial heart.

By "bioactive moiety" is meant a moiety that provides biological activity, e.g., biocidal, anti-inflammatory, or enzymatic activity, or that presents binding or labeling moiety, e.g., for the specific binding of a protein, nucleic acid, carbohydrate, or cell. Exemplary compounds that may be used as bioactive moieties are proteins, nucleic acids, antibiotics, immunosuppressant drugs, anti-inflammatory compounds, antibacterial or antifungal compounds, enzymes, enzyme substrates, enzyme inhibitors, antibodies, organic compounds (natural or synthetic), fluorophores, chromophores, and redox active compounds.

By "thioether" is meant a compound having a sulfur atom bound to two carbon atoms. Exemplary thioethers of the invention are oligomeric or polymeric thioethers, such as block copolymers.

Others features and advantages of the invention will be apparent from the following description and the claims.

BRIEF DESCRIPTION OF THE DRAWINGS

FIGS. 10A-J are a set of pictures showing cell culture experiments with HFFs: step 1) Bare substrates modified with PPS-PEG in methanol, step 2) Other bare substrates served as controls, step 3) Substrates rinsed in methanol, step 4) Solution changed in HEPES buffer, step 5) HFF cells plated on 3 samples of each surface for 20 hours at an approximate cell density of 20,200 cells/ml, step 6) Surface rinsed in buffer, step 7) Multiple randomly spaced images of each surface acquired, step 8) Non-adhesive surfaces subjected to a second plating of HFFs for 20 hours at an approximate cell density of 20,000 cells/ml, and step 9) Surfaces rinsed in buffer and images acquired again.

DETAILED DESCRIPTION OF THE INVENTION

The present invention provides methods and apparatus for coating hydrophobic surfaces, e.g., gold, silver, or copper surfaces, with amphiphilic poly or oligo(thioether) surface coatings that desirably reduce protein adsorption and/or cell adhesion. We developed a new <sulfamer> block copolymer that is useful for non-adhesive chemistry, consisting of asymmetric PEG chains separated by a poly(propylene sulfide) (PPS) block. Poly(ethylene glycol) (PEG) has been used in numerous biomedically motivated systems to aid in minimization of protein adsorption and cell adhesion. The poly(thioether) is extremely hydrophobic, while the PEG side chains are hydrophilic. The material is more versatile than typical alkane thiol self-assembled monolayers (SAMs) and can form films as well as vesicles.

Figure 1:
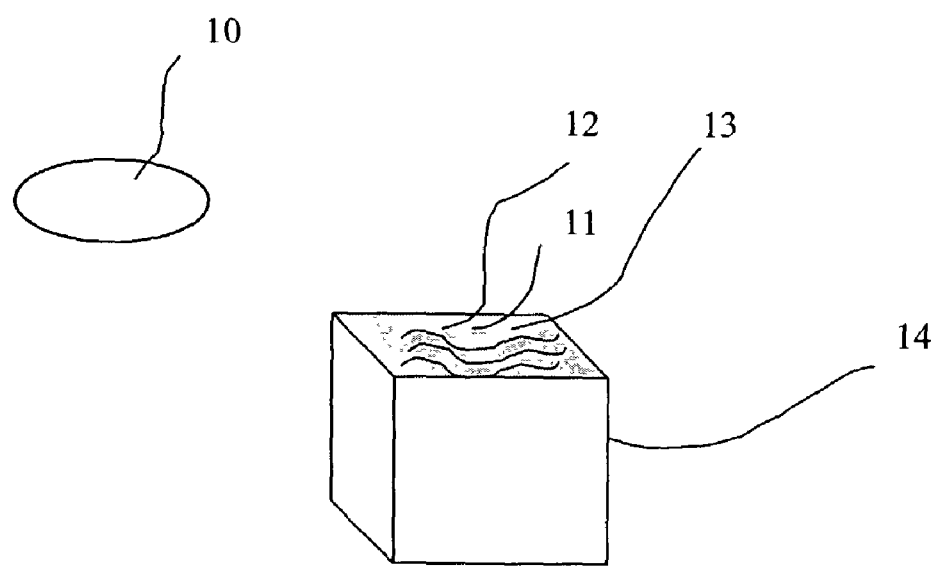
FIG. 1 is a schematic illustration of apparatus for coating surfaces to reduce protein adsorption and cell adhesion.

With reference to FIG. 1, an apparatus for coating surfaces is described. Surface 10, which is desirably hydrophobic, e.g., a metal such as gold, silver, or copper, is contacted with reagent 12, which includes solvent 11 and amphiphilic thioether 13. For the purposes of the present invention, the term "thioether" encompasses poly or oligo(thioethers). Reagent 12 is disposed in vessel 14 and may be, for example, a colloidal suspension of the thioether in water or methanol, or a solution of the thioether in methylene chloride or tetrahydrofuran ("THF"). Other solutions or suspensions will be apparent to those of skill in the art. For rendering surfaces resistant to protein and/or cell adhesion, amphiphilic thioether 13 is, for example, a block copolymer of poly(propylene sulfide) and poly(ethylene glycol) ("PPS-PEG"), as described herein, but other thioethers may be used.

Surface 10 is maintained in reagent 12 for a period of time sufficient to adsorb thioether 13 to the surface. Hydrophobic interactions between the thioether and the surface may facilitate adsorption. Surface 10 is then removed from vessel 14 and optionally may be rinsed to remove excess reagent 12. Adsorbed thioether 13 modifies surface 10 in a reproducible manner, thereby providing a surface 10 that may be engineered for a specific application. Potential applications include, for example, use in a biosensor, use in a protein or cell-containing environment, corrosion prevention, interfacial adhesion promoters to coatings, lubrication, presentation of different chemical functional groups to an interface for molecular recognition, surface patterning, and alteration of surface charges and energetics.

Advantageously, surfaces coated with amphiphilic thioethers in accordance with the present invention are expected to exhibit reduced protein adsorption and/or cell adhesion compared to an uncoated surface. The degree of reduction in protein adsorption or cell adhesion may be controlled, for example, through pendant chain spacing of the thioether. Pendant chains are typically groups attached at the ends of a poly(thioether) block. The length of the thioether backbone may be shortened or lengthened to shorten or lengthen the spacing between pendant chains. Other architectures can readily be envisioned, including multiblock copolymers, amphiphilic copolymers with thioether domains, and thioether backbones with multiple pendant hydrophilic side chains.

Controlling pendant chain length may reduce protein adsorption or cell adhesion, for example, by increasing the surface coverage by the hydrophilic, protein-repellant chains or by altering the surface exposure of the pendant chains. The extent of surface coverage may not necessarily be linked to molecular conformation as it may depend on the weight fraction of the pendant chains occupying the surface. Surface exposure may be altered directly by a change in molecular conformation of the pendant chains. Coverage of the surface by pendant chains may also be influenced by the length of the pendant chains and of the thioether backbone. The length of the pendant chains and/or thioether backbone may be controlled by affecting a degree of polymerization. Techniques for achieving thioether polymerization are described in U.S. application Ser. No. 09/586,937, filed Jun. 2, 2000, now U.S. Pat. No. 6,958,212 and U.S. application Ser. No. 09/496,231, filed Feb. 1, 2000. It is also expected that controlling the surface density of the adsorbed thioether may be used to control the extent of surface coverage. Individual blocks in a block copolymer thioether of the invention may include, for example, on average 5-100 monomer units, 5-75 monomer units, 5-50 monomer units, 5-25 monomer units, 5-10 monomer units, 10-75 monomer units, 10-50 monomer units, 10-40 monomer units, 10-30 monomer units, 10-25 monomer units, or 10-20 monomer units. In addition, blocks that make up a polymeric thioether of the invention may include a mixture of monomers.

In general, the molecular weights for the polythioether block and the pendant hydrophilic chains depend on each other. For example, if a small polythioether block is used, it is advantageous to use a relatively small pendant chain also, and if a higher molecular weight polythioether is used, then it is possible to go to very high molecular weights of pendant chain(s). There are advantages to using small and moderate molecular weight polythioether chains, as this leads to a higher adsorbed fraction of the surface-binding chain, i.e., fewer loops and trains that may be sterically forced to extend above the surface. With high molecular weight pendant chains, it is not necessary to achieve as high a coverage, on a basis of the polythioether, in order to completely sterically inhibit the approach of a protein or cell to a surface. At lower pendant chain molecular weight, it is in general necessary to ensure a higher coverage to prevent adsorption of biomolecules or cells exposed to the treated surface.

The surface exposure of the pendant chains can also be influenced by the adsorption method, e.g., adsorbing from a homogeneous solution or from a colloidal suspension. A suspension may be formed, for example, through dispersion in liquids that are selective solvents for one or more of the blocks and non-solvents for the rest of the polymeric species. Colloidal suspensions may also change the kinetics of hydrophobic interaction with the substrate. Other techniques for altering pendant chain spacing will be apparent to those of skill in the art.

Figure 2A:
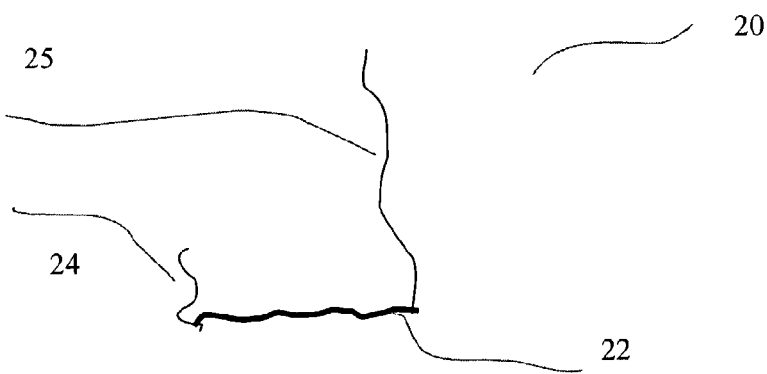
FIGS. 2A-2D are schematic illustrations of the PPS-PEG thioether.
Figure 2B:
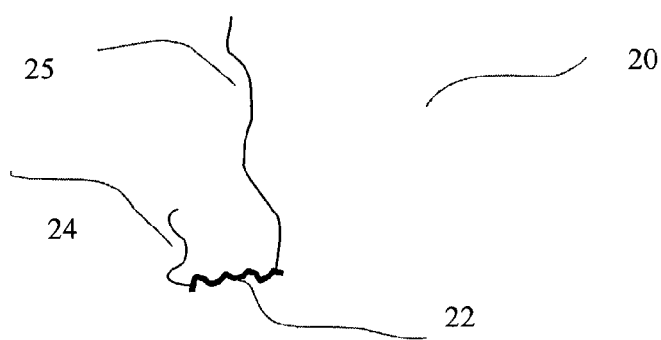
Figure 2C:
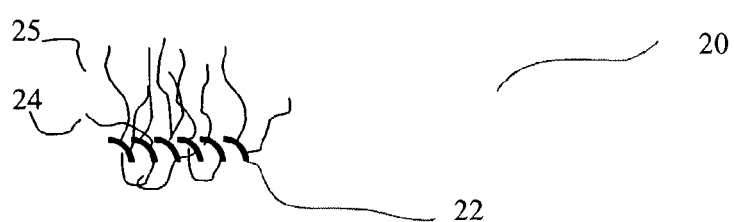
Figure 2D:
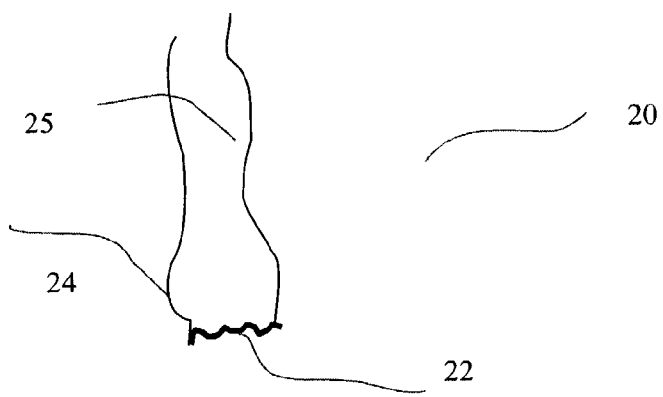

Referring now to FIGS. 2A-2D, schematic representations of techniques for reducing protein adsorption and/or cell adhesion are described with respect to the PPS-PEG polymer. In FIG. 2A, a schematic representation of the molecular structure of PPS-PEG is provided. PPS-PEG molecule 20 includes hydrophobic backbone 22 and attached pendant chains 24 and 25. As discussed previously, the length and/or spacing of pendant chains 24 and 25 may be controlled, for example, to change the exposure of hydrophilic blocks to a water environment and therefore change protein adsorption and/or cell adhesion. In FIG. 2B, the length of backbone 22, is made shorter, for example, by controlling the extent of polymerization, to reduce the spacing between pendant chains 24 and 25. In FIG. 2C, the backbone 20 has been aggregated, for example, by dispersion into a colloidal suspension, thereby effectively shortening the length of backbone 20 and the spacing of pendant chains 24 and 25. Finally, with respect to FIG. 2D, the lengths of pendant chains 24 and 25 have been altered, for example, by controlling the degree of polymerization.

A desired pendant chain spacing and/or length for a given surface may be determined through empirical experimentation and/or theoretical calculations. It is also expected that graphs, tables, databases and the like, may be provided from which desired pendant chain spacing/length, thioether polymerization degree, solution morphology (i.e., such as colloidal suspension), etc. may be readily obtained. A particular chain spacing/length may allow, for example, a reduction in protein adsorption or cell adhesion on a given surface.

Certain characteristics of the poly(thioether) block may be specified. In the case of thioether binding to metal surfaces such as gold, silver, or copper, the sulfur atom is typically exposed to permit chemisorption to the metal surface. As such, a backbone possessing numerous bulky pendant groups can be disadvantageous. In order to permit chemisorption, the backbone is typically dispersed in a liquid environment, for example, through dispersion in a colloidal suspension or micellar aggregates.

In the case of the thioether binding to hydrophobic surfaces, it is desirable that the thioether block retains hydrophobicity. As such, a backbone possessing numerous hydrophilic pendant groups (either side chains or main chain blocks) can be disadvantageous. The thioether moiety is very hydrophobic, and the neighboring pendant moieties preferably do not overwhelm the hydrophobicity of this moiety to generate a more generally hydrophilic environment. Exemplary thioethers include those disclosed in U.S. application Ser. No. 10/047,404, filed Oct. 19, 2001.

Certain characteristics of the other blocks in the block copolymer also may be specified. Given that protein adsorption is dominated by hydrophobic interactions, it is advantageous if the non-thioether block is strongly hydrophilic. Given that most proteins and cell surfaces are net negatively charged, this block may also be negatively charged, as can be achieved, for example, with heparin, hyaluronic acid, numerous polysaccharides, poly(styrene sulfate), poly(styrene sulfonate), poly(acrylic acid), dextran sulfate, and copolymers thereof. Other compositions are readily apparent to those skilled in the art. More desirably, the non-thioether block is water-soluble and nonionic, such as poly(ethylene glycol), poly(hydroxyethyl methacrylate), poly(N-vinyl pyrrolidone), poly(vinyl alcohol), poly(acrylamide), poly(N,N-dimethyl acrylamide), poly(N-isopropyl acrylamide), or poly(N-hydroxypropyl methacrylamide).

The surface coatings of the invention may also be used to present various moieties at an interface. For example, a surface coating may present a biological recognition ligand or a bound drug. When a recognition ligand is employed, the surface coating acts to prevent non-specific adsorption to the surface. The thioether may contain an attachment site, e.g., an amine group or activated ester, for such moieties, which may deposited on the surface with the thioether or attached to thioether already adsorbed on a surface. When the surface-coating is in contact with water, the attachment site may be on the hydrophilic pendant chains. Techniques for achieving such coupling are described, for example, in U.S. application Ser. No. 09/586,937, filed Jun. 2, 2000 and U.S. application Ser. No. 09/496,231, filed Feb. 1, 2000.

The methods and apparatus of the present invention will now be demonstrated through a series of examples. These examples should in no way be considered limiting. Clearly, additional coatings, coating conditions, techniques, etc. will be apparent to those of skill in the art in view of these examples and the disclosure provided herein. It should be understood that all such changes and modifications that fall within the true scope and spirit of the present invention are included in the present invention.

EXAMPLE 1

Surface Passivation of Hydrophobic Materials

PPS-PEG block copolymers were synthesized from a PEG thioacetate block of approximately 16 units. Deprotection of the macrothiol, followed by propyl sulfide living end polymerization, led to a second block of 25 PPS units. End capping with an acrylate PEG of 7 units provided an asymmetric triblock copolymer. The polymer was added to methanol (1 mg/ml) and sonicated to create a translucent colloidal dispersion. The dispersion was first applied to hydrophobic and hydrophilic surface coatings on waveguides suitable for Optical Waveguide Light Spectroscopy (OWLS) to quantify protein adhesion of human serum albumin (HSA) and/or serum. PPS-PEG (e.g., $EG_{16}PS_{25}EG_8$ or $EG_{16}PS_{25}EG_7$ triblock, the subscript denotes the number of repeating units of the monomers) was deposited for 30 minutes on a hydrophobic surface, modified polytetrafluoroethylene (e.g., "Teflon AF 1600")-coated or an alkane phosphate (e.g., octadecylphosphate ("ODP"))-coated metal or metal oxide surface (e.g., Au, $TiO_2$, or SiTi sol gel coating) (Tables 1 and 2), from a colloidal suspension in methanol at 1 mg/ml. The PPS-PEG alternatively could have been deposited by a variety of other techniques, for example, from a dispersion in water or a solution in dichloromethane. Once PPS-PEG was deposited, and the surface was rinsed in methanol and then in HEPES Z1 buffer, the surface was exposed to one or more proteins, for example, HSA or blood serum. Control hydrophobic surfaces without the PPS-PEG were also exposed to proteins.

TABLE 1

| XPS Elemental Composition for Substrates and PPS-PEG | | | | | | | | | |
|---|---|---|---|---|---|---|---|---|---|
| At % | Bare Au | PPS-PEG on Au | norm. | Theor. PPS-PEG | ODP on $TiO_2$ | norm. | Theor. ODP | $TiO_2$ | PS | TCPS |
| C | 13.5 | 63.2 | 72.4 | 72.3 | 50.8 | 75.8 | 78.3 | 11.1 | 100 | 86.4 |
| O | 3.6 | 10.1 | 11.6 | 10.8 | 36.0 | 20.9 | 17.4 | 56.9 | | 13.6 |
| S | | 14.0 | 16.0 | 16.9 | | | | | | |
| Au | 82.8 | 12.7 | | | | | | | | |
| P | | | | | 2.2 | 3.3 | 4.3 | | | |
| Ti | | | | | 11.0 | | | 32.0 | | |

TABLE 2

PPS-PEG Adsorption on Substrates

| Substrate | PPSPEG (ng/cm$^2$) |
|---|---|
| Au | 303.4 ± 34.6 |
| ODP | 94.7 ng/cm$^2$ ± 4.7 |
| $TiO_{2\ (control)}$ | 189.0 ng/cm$^2$ ± 21.9 |

Figure 3:
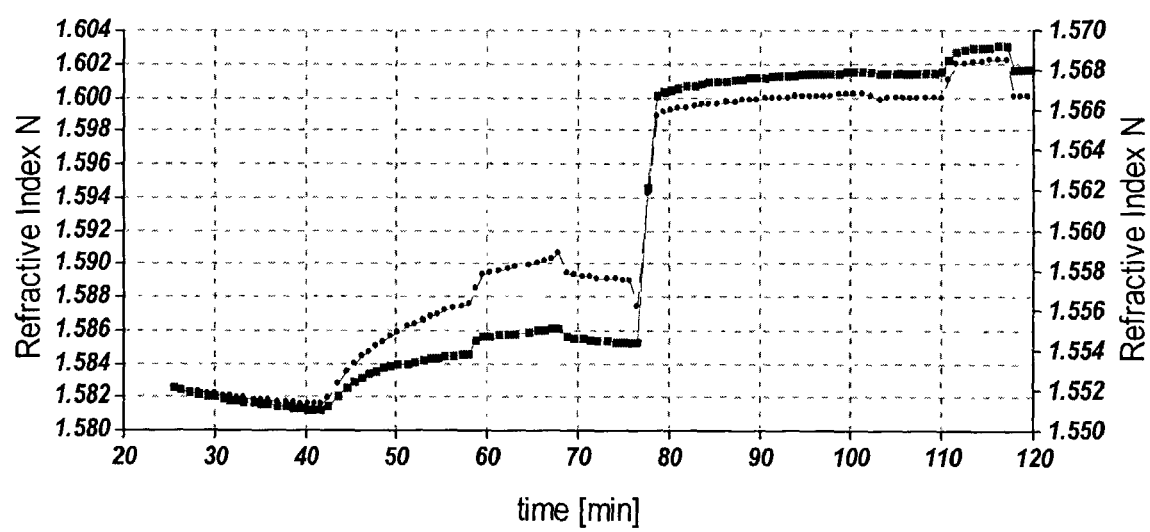
FIG. 3 is a graph of optical waveguide light spectroscopy ("OWLS") quantifying protein adsorption. PPS-PEG adsorbed on a Teflon AF coated waveguide shows no protein adsorption according to OWLS: step 1) methanol baseline, step 2) PPS-PEG adsorption, step 3) transition from methanol to HEPES buffer, step 4) no HSA adsorption, and step 5) no serum adsorption (level back to aqueous baseline upon rinse with HEPES).
Figure 8:
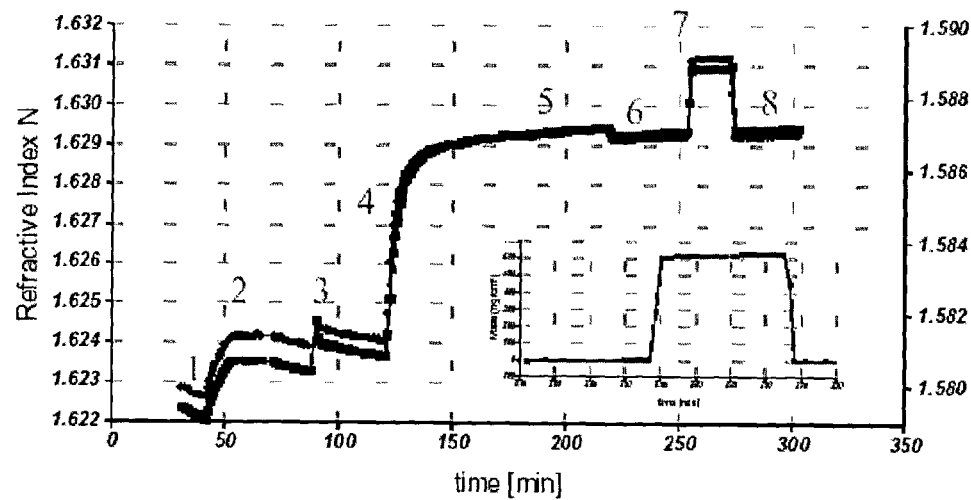
FIG. 8 is a graph of OWLS quantifying protein adsorption: step 1) ODP coated waveguide in methanol, step 2) PPS-PEG adsorbed on ODP in Methanol, step 3) Methanol rinse, step 4) Solution changed to HEPES buffer, step 5) HSA injection, step 6) HEPES flush, step 7) Serum injection, and step 8) HEPES flush (note: inset curve shows adsorption (mass vs. time) for serum injection and rinse).
Figure 9:
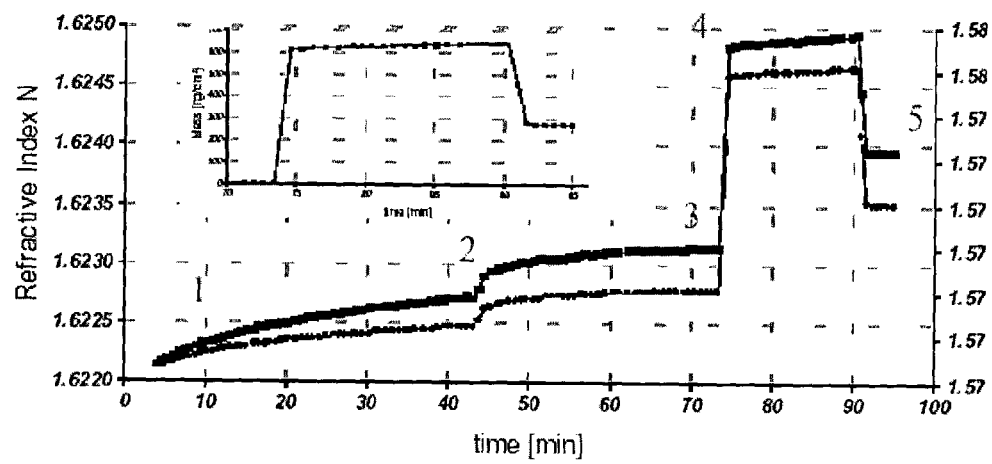
FIG. 9 is a graph of OWLS quantifying protein adsorption: step 1) Bare ODP coated waveguide in HEPES buffer, step 2) HSA injection and adsorption, step 3) HEPES flush, step 4) Serum injection and adsorption, and step 5) HEPES flush (note: inset curve shows adsorption (mass vs time) for serum injection and rinse).

Tables 3 and 4 show results of the above experiment. Control Teflon AF-coated surfaces adsorbed approximately 160 ng/cm$^2$ of HSA, while control alkane phosphate-coated surfaces adsorbed approximately 100 ng/cm$^2$ of HSA. Conversely, alkane phosphate- and Teflon AF-coated surfaces, with applied PPS-PEG, adsorbed less protein than detectable by the testing system employed (<2 ng/cm$^2$). PPS-PEG therefore serves as a passivating treatment for hydrophobic surfaces against protein adsorption. FIGS. 3, 8, and 9 show an OWLS plot of polymer adsorption, change in refractive index between methanol and HEPES buffer, and lack of HSA and serum adsorption (complete removal was observed upon a HEPES rinse). These results indicate that PPS-PEG applied to hydrophobic, but not hydrophilic surfaces, renders surfaces both protein and cell resistant.

TABLE 3

Protein adsorption (HSA) measured with OWLS on PPSPEG treated and control substrates.

| Substrate | Treatment | HSA (ng/cm$^2$) |
|---|---|---|
| Teflon AF | PPSPEG | — |
| Teflon AF | control | 160 |
| ODP | PPSPEG | — |
| ODP | control | 107 |
| SiTi | PPSPEG | replacement |
| SiTi | control | 176 |

TABLE 4

Protein adsorption on treated and untreated surfaces.

| Substrate | HSA (ng/cm$^2$) | Serum (ng/cm$^2$) |
|---|---|---|
| Au | | 580 ± 100 |
| Au + PPSPEG | — | 25.3 ± 16.8 |
| ODP | 100.7 ± 6.9 | 229.8 ± 40.0 |
| ODP + PPSPEG | — | 2.6 ± 4.5 |
| $TiO_{2\ (control)}$ | 200.0 ± 5 | 378.0 ± 31.0 |
| $TiO_{2\ (control)}$ + PPSPEG | | 189.3 ± 113.5 |

Figure 4:
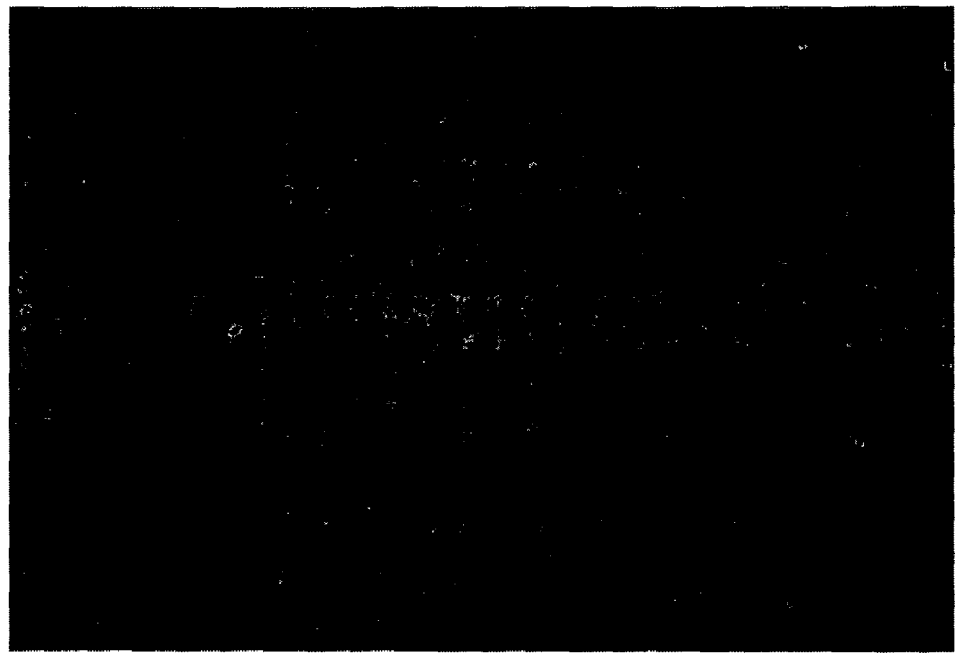
FIG. 4 is a picture demonstrating reduced cell adhesion on polystyrene coated with PPS-PEG.
Figure 5:
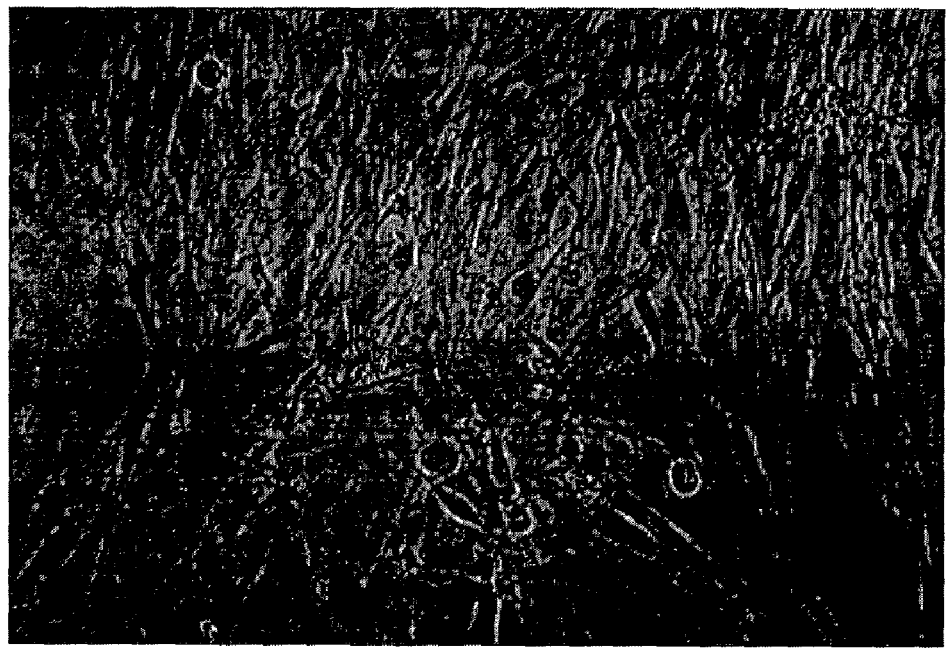
FIG. 5 is a picture demonstrating significant cell adhesion on tissue culture polystyrene ("TCPS").
Figure 11:
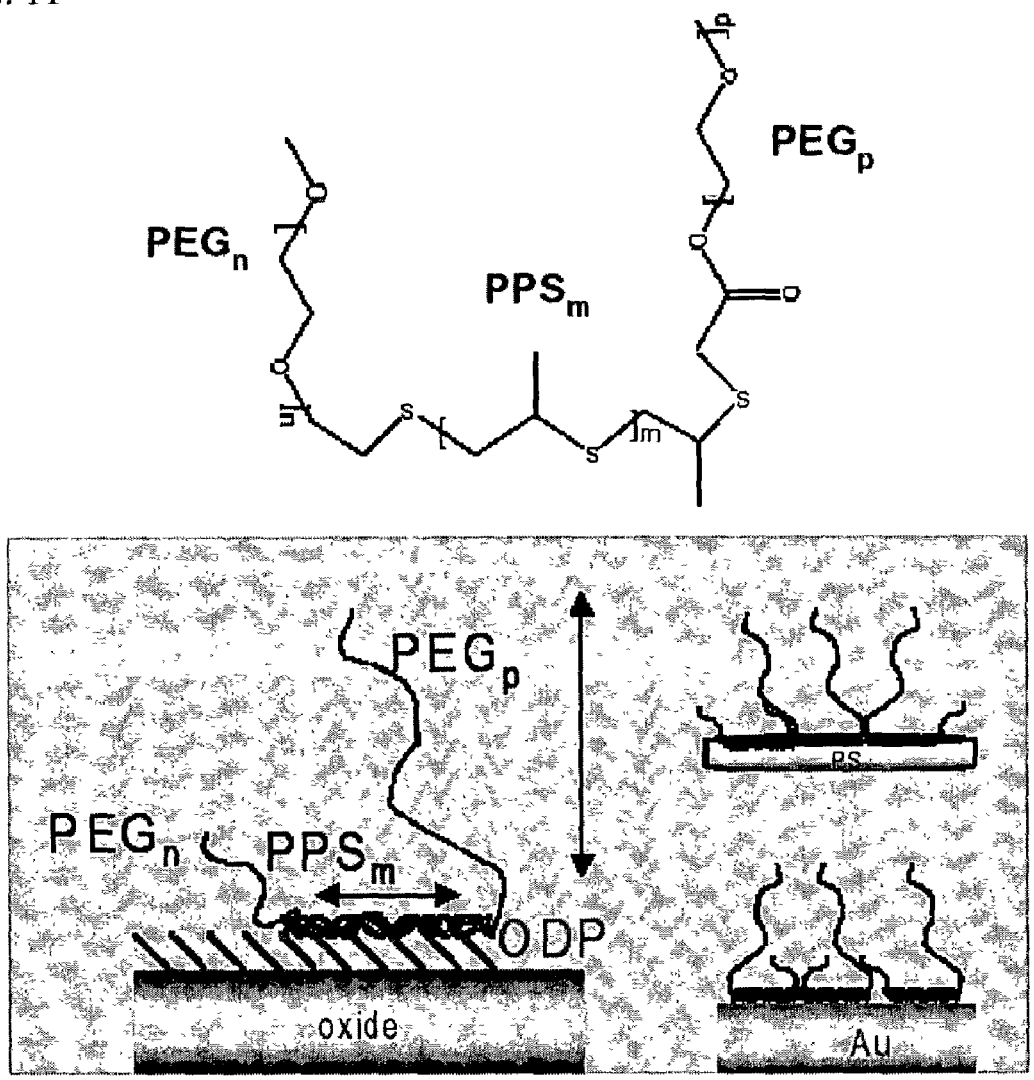
FIG. 11 is a picture showing the structure of PPS-PEG bound and unbound to surfaces.

The PPS-PEG coating was next applied in a similar fashion to Teflon, dodecyl phosphate, $SiO_2$, and tissue culture polystyrene ("TCPS") to test the effect of plating Human Foreskin Fibroblasts ("HFF") for 20 hours at a seeding density of approximately 20,000 cells per culture dish well. Cells grown on TCPS served as a control. As seen in FIG. 4, PPS-PEG adsorbed on polystyrene showed virtually no cell attachment. However, as seen in FIG. 5, HFFs attached and rapidly multiplied on TCPS surfaces. PPS-PEG adsorbed from a colloidal dispersion therefore acts as a passivating treatment towards cell adhesion, as well as protein adsorption. PPSPEG adsorbed from methanol onto hydrophobic surfaces rendered all surfaces tested protein and cell resistant for at least 20 hours. FIGS. 10A-10J and Table 5 show results for Au, ODP, PS, TCPS, and $TiO_2$ surfaces with and without the PPS-PEG coating. FIG. 11 shows a schematic illustration of the PPS-PEG bound and unbound to a surface.

TABLE 5

Density of cells adhered to coated and uncoated surfaces.

|  | Au | | | ODP | | | PS | | |
| --- | --- | --- | --- | --- | --- | --- | --- | --- | --- |
|  | Plating 1 | Plating 2 | Control | Plating 1 | Plating 2 | Control | Plating 1 | Plating 2 | Control |
| Density (cells/mm$^2$) | 3.6 ± 2.7 | 6.0 ± 5.7 | 249.2 ± 219.8 | 8.9 ± 8.4 | 21.4 ± 21.7 | 26.4 ± 14.9 | 0.7 ± 0.2 | 0.8 ± 0.3 | 54.0 ± 29.1 |
| Area/cell ($\mu m^2$) | 178.8 ± 109.1 | 467.4 ± 356.4 | 2206.4 ± 1276.8 | 325.8 ± 283.1 | 545.0 ± 505.4 | 1793.2 ± 1268.9 | n.a. | n.a. | 632.4 ± 568.2 |

|  | TiO$_2$ | | TCPS | |
| --- | --- | --- | --- | --- |
|  | Plating 1 | Control | Plating 1 | Control |
| Density (cells/mm$^2$) | 330.5 ± 162.0 | 423.6 ± 239.3 | 109.4 ± 86.5 | 168.0 ± 72.4 |
| Area/Cell ($\mu m^2$) | 1614.0 ± 1327.8 | 2346.0 ± 1663.4 | 2274.3 ± 1682.1 | 2346.0 ± 1663.3 |

EXAMPLE 2

Surface Passivation on Metals

PPS-PEG (e.g., EG$_{16}$PS$_{25}$EG$_8$ triblock) was deposited on a gold or copper surface from a colloidal suspension in methanol at 1 mg/ml, to examine resistance to protein adsorption. Alternatively, the PPS-PEG could be deposited by a variety of other techniques, for example, from a dispersion in water or a solution in dichloromethane. Once PPS-PEG was deposited, the surface was exposed to one or more proteins, for example, HSA or serum. Control gold surfaces without the PPS-PEG were also exposed to proteins.

Figure 6:
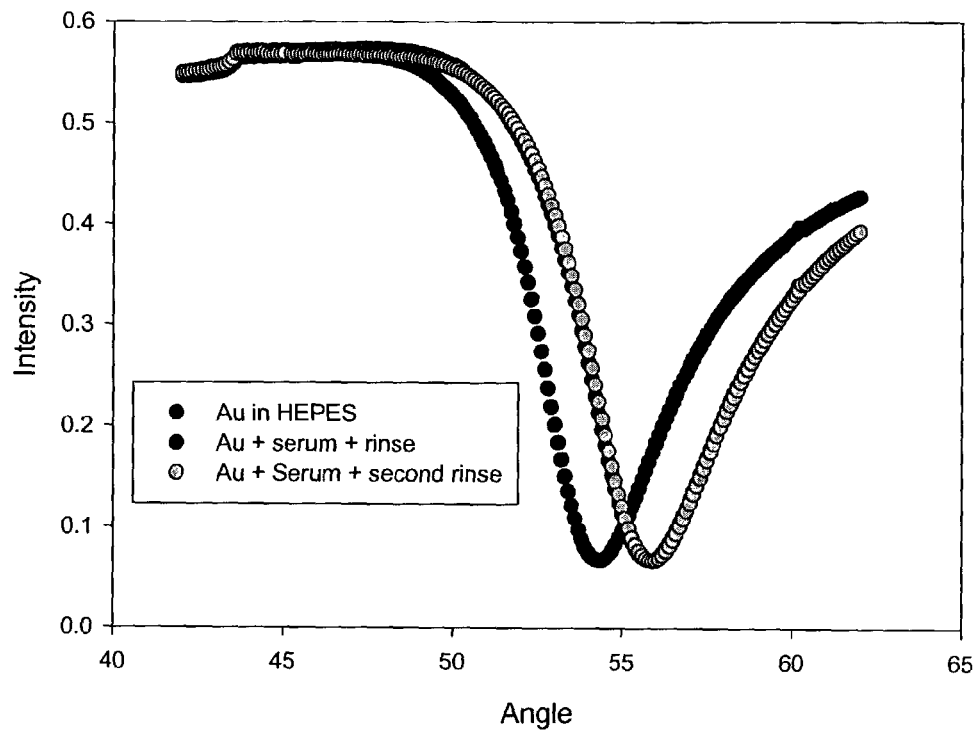
FIG. 6 is a graph of surface plasmon resonance ("SPR") data demonstrating a shift in incidence angle due to protein adsorption on a bare gold substrate.
Figure 7:
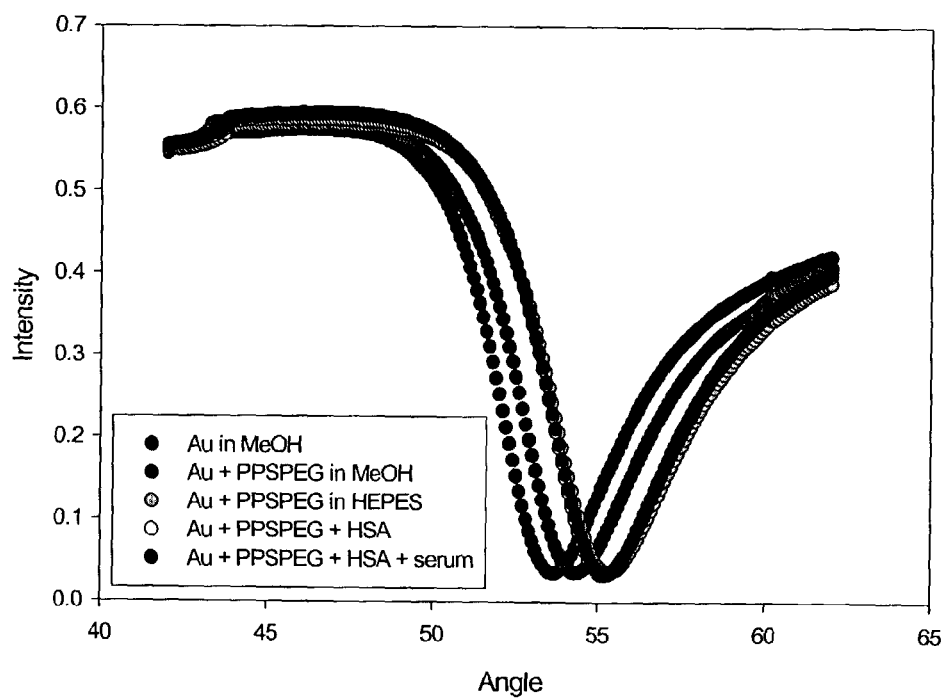
FIG. 7 is a graph of SPR data showing a shift in incidence angle due to PPS-PEG adsorption on a bare gold substrate, followed by a reduced shift in incidence angle due to reduced protein adsorption.

With reference to FIG. 6, control gold surfaces adsorbed approximately 580 ng/cm$^2$ of serum proteins, as demonstrated by a significant shift in incidence angle. Referring to FIG. 7, PPS-PEG-coated gold surfaces adsorbed undetectable amounts of HSA and approximately 25 ng/cm$^2$ of serum proteins, as demonstrated by the shifts in angle of incidence. PPS-PEG adsorbed from a colloidal dispersion therefore served as a passivating treatment for metallic surfaces against protein adsorption.

REFERENCES

Adsorption of Bifunctional Organic Disulfides on Gold Surfaces. R. G. Nuzzo and D. L. Allara, *J. Am. Chem. Soc.,* 1983, 105, 4481-4483.
Fundamental Studies of the Chemisorption of Organosulfur Compounds on Au(111). Implications for Molecular Self-Assembly on Gold Surfaces. R. G. Nuzzo, B. R. Zegardki, and L. H. Dubois, *J. Am. Chem. Soc.,* 1987, 109, 773-740.
Self-Assembled Monolayers on Gold Generated from Alkanthiols with the Structure RNHCOCH$_2$SH. S. W. Tam-Chang, H. A. Biebuyck, G. M. Whitesides, N. Jeon, and R. G. Nuzzo. *Langmuir,* 1995, 11, 4371-4382.
Contact-Inking Stamps for Microcontact Printing Alkanethiols on Gold. L. Libioulle, A. Bietsch, H. Schmid, B. Michel, and E. Delamarche, *Langmuir,* 1999, 15, 300-304.

OTHER EMBODIMENTS

From the foregoing description, it will be apparent that variations and modifications may be made to the invention described herein to adopt it to various usages and conditions.

All publications, patent applications, and patents mentioned in this specification are hereby incorporated by reference.

Other embodiments are in the claims.

What is claimed is:

1. A coating on a substrate surface, said coating comprising an amphiphilic thioether coated on a hydrophobic surface of a substrate, wherein said thioether comprises a hydrophilic pendant group, and wherein said coating renders said surface more hydrophilic than an uncoated surface, wherein said thioether is PEG$_{16}$PPS$_{25}$PEG$_7$ or PEG$_{16}$PPS$_{25}$PEG$_8$.

2. The surface coating of claim 1, wherein said substrate is a metal.

3. The surface coating of claim 2, wherein said metal is gold, silver, or copper.

4. The surface coating of claim 1, wherein said thioether is adsorbed onto said hydrophobic substrate.

5. The surface coating of claim 4, wherein said thioether is adsorbed from a solution or colloidal dispersion.

6. The surface coating of claim 1, wherein said surface coating reduces protein adsorption or cell adhesion on said substrate compared to said substrate without said coating.

7. The surface coating of claim 1, further comprising a bioactive moiety covalently linked to said thioether.

8. The surface coating of claim 7, wherein said bioactive moiety comprises an organic compound, a nucleic acid, a protein, an enzyme substrate, an enzyme inhibitor, or an antibody.

9. The surface coating of claim 7, wherein said bioactive moiety covalently linked to said thioether is hydrolyzed from said thioether with a half-life of between 1 hour and 1 year at pH 7.4 and 37° C.

10. The surface coating of claim 7, wherein said bioactive moiety is linked to said thioether through an amide or ester bond.

11. The surface coating of claim 1, wherein said surface is the surface of a medical device.

12. A method of coating a surface, said method comprising coating said surface with an amphiphilic thioether, wherein said thioether comprises a hydrophilic pendant group, and wherein said pendant group causes a reduction in protein adsorption or cell adhesion relative to an uncoated surface, wherein said thioether is PEG$_{16}$PPS$_{25}$PEG$_7$ or PEG$_{16}$PPS$_{25}$PEG$_8$.

13. The method of claim 12, wherein said surface is a hydrophobic surface.

14. The method of claim 12, wherein said surface comprises gold, silver, or copper.

15. The method of claim 12, wherein said coating comprises adsorbing said amphiphilic thioether from a solution or colloidal suspension.

16. The method of claim 12, wherein protein adsorption or cell adhesion is reduced by at least 90% relative to an uncoated surface.

17. The method of claim 12, wherein protein adsorption of cell adhesion is reduced by at least 95% relative to an uncoated surface.

18. The method of claim 12, wherein said thioether is covalently linked to a bioactive moiety.

19. The method of claim 18, wherein said bioactive moiety comprises an organic compound, a nucleic acid, a protein, an enzyme substrate, an enzyme inhibitor, or an antibody.

20. The method of claim 18, wherein said bioactive moiety covalently linked to said thioether is hydrolyzed from said thioether with a half-life of between 1 hour and 1 year at pH 7.4 and 37° C.

21. The method of claim 18, wherein said bioactive moiety is linked to said thioether through an amide or ester bond.

22. The method of claim 12, wherein said surface is the surface of a medical device.

* * * * *